(12) United States Patent
Cardosi et al.

(10) Patent No.: US 10,371,617 B2
(45) Date of Patent: Aug. 6, 2019

(54) ELECTROCHEMICAL TEST DEVICE

(71) Applicant: Inside Biometrics Limited, Dingwall (GB)

(72) Inventors: Marco Cardosi, Dingwall (GB);
Stephanie Kirkwood, Dingwall (GB);
Damian Baskeyfield, Dingwall (GB)

(73) Assignee: INSIDE BIOMETRICS INTERNATIONAL LIMITED, Dingwall (GB)

( * ) Notice: Subject to any disclaimer, the term of this patent is extended or adjusted under 35 U.S.C. 154(b) by 82 days.

(21) Appl. No.: 15/569,730

(22) PCT Filed: Apr. 28, 2016

(86) PCT No.: PCT/GB2016/051231
§ 371 (c)(1),
(2) Date: Oct. 26, 2017

(87) PCT Pub. No.: WO2016/174458
PCT Pub. Date: Nov. 3, 2016

(65) Prior Publication Data
US 2018/0128727 A1 May 10, 2018

(30) Foreign Application Priority Data
Apr. 30, 2015 (GB) .................... 1507508.8

(51) Int. Cl.
*G01N 15/06* (2006.01)
*G01N 27/327* (2006.01)
*C12Q 1/00* (2006.01)

(52) U.S. Cl.
CPC ......... *G01N 15/0656* (2013.01); *C12Q 1/005* (2013.01); *C12Q 1/006* (2013.01); *G01N 27/327* (2013.01); *G01N 27/3272* (2013.01)

(58) Field of Classification Search
CPC ....... G01N 15/0656; G01N 2015/1062; G01N 2015/1486; G01N 17/02; G01N 27/26;
(Continued)

(56) References Cited

U.S. PATENT DOCUMENTS

| 5,556,533 A * | 9/1996 | Nozoe | C12Q 1/001 |
| | | | 204/412 |
| 7,357,851 B2 * | 4/2008 | Reid | G01N 27/3272 |
| | | | 204/403.04 |

(Continued)

FOREIGN PATENT DOCUMENTS

| EP | 2292785 A1 | 3/2011 |
| EP | 2308991 A1 | 4/2011 |

(Continued)

OTHER PUBLICATIONS

International Search Report and Written Opinion dated Jul. 21, 2016 for corresponding International Patent Application No. PCT/GB2016/051231.

(Continued)

*Primary Examiner* — Hoai-An D. Nguyen
(74) *Attorney, Agent, or Firm* — Tarolli, Sundheim, Covell & Tummino LLP

(57) ABSTRACT

An electrochemical test device for determining a concentration of one or more analytes in a fluid sample is provided. The electrochemical test device comprises a set of electrodes including two or more working electrodes, each working electrode for determining the concentration of a corresponding analyte, and sensing chemistry for each working electrode, wherein the sensing chemistry for a first of the two or more working electrodes comprises a diaphorase, an electron transfer agent, an NAD(P)$^+$-dependent dehydrogenase and a cofactor for the NAD(P)$^+$-dependent dehydrogenase, wherein at least some of the diaphorase for the first working electrode is disposed in a diaphorase-containing layer which (Continued)

extends over the first working electrode and at least a second of the two or more working electrodes.

20 Claims, 5 Drawing Sheets

(58) Field of Classification Search
CPC .............. G01N 27/327; G01N 27/3271; G01N 27/3272; G01N 27/3275; G01N 33/48735; G01N 33/5438; C12Q 1/00; C12Q 1/001; C12Q 1/005; C12Q 1/006; G02B 5/3008; G01R 31/12
USPC .......... 324/71.1, 71.4; 204/193, 194, 196.06, 204/229.8, 400, 403.01, 403.14, 556
See application file for complete search history.

(56) References Cited

U.S. PATENT DOCUMENTS

| | | | | |
|---|---|---|---|---|
| 8,226,814 | B2* | 7/2012 | Mao | C07F 15/0026 204/403.02 |
| 2002/0053523 | A1* | 5/2002 | Liamos | G01N 27/3272 205/787 |
| 2008/0169206 | A1* | 7/2008 | Pei | C12Q 1/005 205/780.5 |
| 2010/0213057 | A1 | 8/2010 | Feldman et al. | |
| 2011/0079522 | A1* | 4/2011 | Webster | C12Q 1/006 205/792 |
| 2016/0202206 | A1* | 7/2016 | Goluch | G01N 27/3275 205/777.5 |
| 2017/0145203 | A1* | 5/2017 | Valint, Jr. | A61B 5/14514 |
| 2017/0273610 | A1* | 9/2017 | Suri | A61B 5/14546 |
| 2017/0285016 | A1* | 10/2017 | Musho | G01N 27/3274 |
| 2018/0143155 | A1* | 5/2018 | Cardosi | C12Q 1/004 |
| 2018/0163246 | A1* | 6/2018 | Saini | C12Q 1/005 |

FOREIGN PATENT DOCUMENTS

| | | |
|---|---|---|
| EP | 2317313 A1 | 5/2011 |
| GB | 2337122 A | 11/1999 |
| WO | 2011030093 A1 | 3/2011 |

OTHER PUBLICATIONS

GB Search Report dated Jan. 30, 2016 for corresponding GB Patent Application No. 1507508.8.
Marco Cardosi et al., "Amperometric Glucose Sensors for Whole Blood Measurement Based on Dehydrogenase Enzymes", "Dehydrogenases" Nov. 14, 2012.

* cited by examiner

ELECTROCHEMICAL TEST DEVICE

RELATED APPLICATIONS

The present application is a U.S. National Stage application under 35 USC 371 of PCT Application Serial No. PCT/GB2016/051231, filed on 28 Apr. 2016; which claims priority from GB Patent Application No. 1507508.8, filed 30 Apr. 2015, the entirety of both of which are incorporated herein by reference.

TECHNICAL FIELD

The present invention relates to electrochemical test devices such as test strips for determining the concentration of one or more analytes in a fluid sample. In particular, the present invention relates to sensing chemistry for such electrochemical test devices.

BACKGROUND

The detection and measurement of substances, chemicals, or analytes in a bodily fluid sample is useful in a variety of applications, such as in fitness monitors or in the medical device industry. For example, an individual may choose to monitor a concentration of an analyte such as glycerol in his or her bloodstream in order to determine whether or not a chosen fitness regime is effective. Glycerol is a fitness related analyte associated with lipolysis and fat breakdown from stored body fat.

As another example, people with diabetes need to regularly monitor the concentration of glucose in their bloodstream in order to determine if they are in need of glucose or insulin or other diabetes medication. Diagnostic devices and kits have been developed over the years to allow a diabetic individual to autonomously determine the concentration of glucose in their bloodstream, in order to better anticipate the onset of hyperglycaemia or hypoglycaemia and take any necessary action.

When trying to ascertain a level of an analyte in, for example, a blood sample, an individual will typically perform a finger stick using a lancing device to extract a small drop of blood from a finger or alternative site. An electrochemical test device, which is often a test strip, is then inserted into a diagnostic meter, and the sample is applied to the test strip. Through capillary action, the sample flows through a capillary channel across a measurement chamber of the device and into contact with one or more electrodes or conductive elements coated with sensing chemistry for interacting with a particular analyte or other specific chemical (for example glucose) in the blood sample. The magnitude of the reaction is dependent on the concentration of the analyte in the blood sample. The diagnostic meter may detect the current generated by the reaction of the sensing chemistry with the analyte, and the result can be displayed to the individual.

Typically, such electrochemical test devices have a set of electrodes such as a counter/reference electrode and one or more working electrodes. Sensing chemistry is used which is typically tailored to the particular analyte or biometric of interest. An enzymatic electrode is a combination of an enzyme and an electrochemical transducer. The direct transfer of electrons between the enzyme and the electrode is generally not easy to achieve and so an electron transfer agent (or mediator) is sometimes used to carry electrons between the enzyme and the electrode to facilitate the electrocatalysis. For example, when measuring the concentration of glucose in a sample, a glucose oxidase or a glucose dehydrogenase enzyme can be used in conjunction with a mediator such as potassium ferricyanide. When detecting other analytes, different enzymes may be used, such as p-hydroxybutyrate dehydrogenase for measuring the ketone body β-hydroxybutyrate.

The NAD(P)$^+$-dependent dehydrogenases, such as glycerol dehydrogenase, require nicotinamide adenine dinucleotide (either in its oxidized form, NAD(P)$^+$ or reduced form, NAD(P)H) as a cofactor for the dehydrogenase. Since the dehydrogenases release NAD(P)$^+$/NAD(P)H from active sites reversibly, NAD(P)$^+$/NAD(P)H may function as the electron transfer agent in the dehydrogenase-modified electrodes. The direct oxidation of NAD(P)H at a carbon working electrode requires a large positive overpotential (for example 0.55 V) and so electrochemically active interferents may transfer electrons to the electrode, thereby interfering with the measurement of an analyte.

In a healthy individual, for some analytes such as glycerol or β-hydroxybutyrate the concentrations of the analytes may be very low. Insensitive or inaccurate electrochemical test devices may take unreliable measurements of the concentration of such analytes. For measurements of some analytes, such as glycerol or β-hydroxybutyrate, sensitive electrochemical test devices are desired.

The present invention seeks to provide an improved electrochemical test device for determining a concentration of one or more analytes in a fluid sample.

SUMMARY

An electrochemical test device for determining a concentration of one or more analytes in a fluid sample is provided. The electrochemical test device may comprise a set of electrodes including two or more working electrodes, each working electrode for determining the concentration of a corresponding analyte. The electrochemical test device may comprise sensing chemistry for each working electrode. The sensing chemistry for a first of the two or more working electrodes may comprise a diaphorase. The sensing chemistry for the first of the two or more working electrodes may comprise an electron transfer agent. The sensing chemistry for the first of the two or more working electrodes may comprise an NAD(P)$^+$-dependent dehydrogenase. The sensing chemistry for the first of the two or more working electrodes may comprise a cofactor for the NAD(P)$^+$-dependent dehydrogenase, such as nicotinamide adenine dinucleotide (NAD$^+$) or nicotinamide adenine dinucleotide phosphate (NADP$^+$). At least some of the diaphorase for the first working electrode may be disposed in a diaphorase-containing layer which extends over the first working electrode and at least a second of the two or more working electrodes.

Further optional features will be appreciated from the following description.

BRIEF DESCRIPTION OF THE DRAWINGS

Illustrative embodiments of the present disclosure will now be described, by way of example only, with reference to the drawings. In the drawings.

Throughout the description and the drawings, like reference numerals refer to like parts.

DETAILED DESCRIPTION

Figure 1:
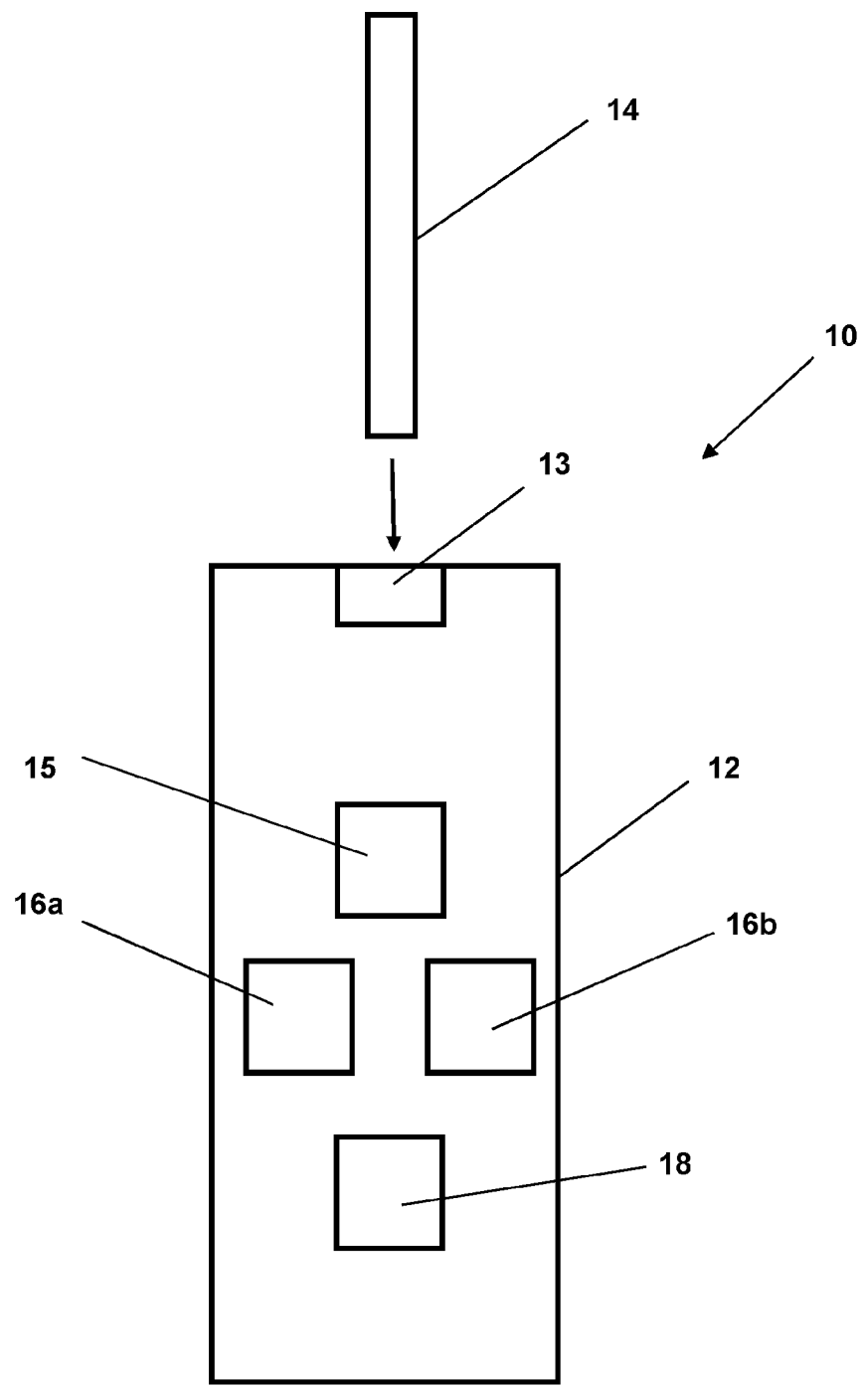
FIG. 1 shows a strip-meter system.

The present invention seeks to provide an improved electrochemical test device for determining a concentration of one or more analytes in a fluid sample. Whilst various embodiments of the invention are described below, the invention is not limited to these embodiments, and variations of these embodiments may be made without departing from the scope of the invention.

Throughout this specification, reference is made to directional terms such as "above" and "below", or "upper" and "lower". References made to such terms are purely indicative of relative positions of the features of embodiments disclosed herein. For example, wherever there is mention of a cover above a spacer layer and an insulator layer below the spacer layer, it should be understood that the cover and the insulator layer are formed on opposite sides of the spacer layer. That is, directional terms such as those described herein do not refer to a direction relative to a viewpoint of an observer, but instead should be considered in all aspects as relative terms.

Various additional details of aspects of electrochemical test devices are described in the following commonly assigned patent applications (denoted collectively herein as the "related applications"). These related applications include the International patent application having attorney reference number P62545WO, entitled "Electrochemical test device" filed on 28 Apr. 2016; the International patent application having attorney reference number P62546WO, entitled "Electrochemical test device" filed on 28 Apr. 2016; the International patent application having attorney reference number P62548WO, entitled "Electrochemical test device" filed on 28 Apr. 2016; the International patent application having attorney reference number P62512WO, entitled "Electron Transfer Agent" filed on 28 Apr. 2016; the International patent application having attorney reference number P62017WO, entitled "System and method for measuring fitness-related parameters" filed on 28 Apr. 2016; and the International patent application having attorney reference number P63023WO, entitled "Electrochemical test device" filed on 28 Apr. 2016. The content of each of these related applications is hereby incorporated by reference herein in its entirety for all purposes.

The term "alkyl", used alone or as part of a larger moiety, refers to a straight or branched chain aliphatic group having from 1 to 12 carbon atoms. The alkyl group therefore has 1, 2, 3, 4, 5, 6, 7, 8, 9, 10, 11 or 12 carbon atoms. For purposes of the present disclosure, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, and hexyl.

The term "amine" may refer to a primary, secondary or tertiary amine. The amine will generally be NRR'R", where R, R' and R" are each selected from hydrogen or alkyl. Any suitable alkyl group may be used. Preferred alkyl group will be $C_1$, $C_2$, $C_3$, $C_4$, $C_5$, $C_6$. Preferably, an amine is $NH_3$.

The term "heteroaryl" means a monocyclic or bicyclic radical of 5 to 12 ring atoms having at least one aromatic ring containing one, two, or three ring heteroatoms selected from N, O or S, the remaining ring atoms being C. The attachment point of the heteroaryl radical may be via the heteroatom. The heteroaryl rings may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

The term "halide" refers to a substituent which is fluoro, chloro, bromo or iodo.

The term "substituted", as used herein, means that a hydrogen radical of the designated moiety is replaced with the radical of a specified substituent, provided that the substitution results in a stable or chemically feasible compound. The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different.

An electron transfer agent (or redox mediator) is an agent for transferring electrons between an analyte or an analyte-reduced or analyte-oxidized enzyme and an electrode, either directly, or via one or more additional electron transfer agents.

An electron transfer agent as disclosed herein may be distinguishable by its standard redox potential i.e. a standard hydrogen electrode (SHE) at Standard Temperature and Pressure (25° C. and 1 atm).

An electrochemical test device for determining a concentration of one or more analytes in a fluid sample is provided. The electrochemical test device comprises a set of electrodes including two or more working electrodes. Each working electrode is for determining the concentration of a corresponding analyte. The electrochemical test device further comprises sensing chemistry for each working electrode. The sensing chemistry for a first of the two or more working electrodes comprises a diaphorase. The sensing chemistry for the first working electrode further comprises an electron transfer agent. The sensing chemistry for the first working electrode further comprises an $NAD(P)^+$-dependent dehydrogenase. The sensing chemistry for the first working electrode further comprises a cofactor for the $NAD(P)^+$-dependent dehydrogenase. At least some of the diaphorase for the first working electrode is disposed in a diaphorase-containing layer which extends over the first working electrode and at least a second of the two or more working electrodes.

The diaphorase may be any suitable diaphorase. For example, the diaphorase may be an NADPH:acceptor oxidoreductase (NADPH dehydrogenase of the class EC 1.6.99.1). The diaphorase may be an NADH:acceptor oxidoreductase (NADH dehydrogenase of the class EC 1.6.99.3). The diaphorase may be an NADH:(quinone acceptor) oxidoreductase (NADH dehydrogenase (quinone) of the class EC 1.6.99.5).

The cofactor may be nicotinamide adenine dinucleotide (NAD$^+$). The cofactor may be nicotinamide adenine dinucleotide phosphate (NADP$^+$).

By providing at least some of the diaphorase in a diaphorase-containing layer which extends over the first working electrode and at least a second of the working electrodes, the production process of an electrochemical test device with multiple working electrodes is simplified, as a common diaphorase-containing layer may be provided, without the need for individually mixing with the reagents of other layers.

Furthermore, by providing a diaphorase-containing layer which extends across multiple working electrodes, the relevant reactions for each analyte to be detected by the electrochemical test device can be localised by the provision of further reagent layers at the relevant electrode. Such layering allows the suited microenvironments to be tailored to each dehydrogenase as required with the selective presence of buffers, pH, enzyme stabilisers, other stabilisers and so on.

Furthermore, if the diaphorase is provided only in the diaphorase-containing layer, then a diaphorase-stabilising enzyme such as flavin mononucleotide (FMN) need not be present in any analyte-sensitive layers. If a mediator is used that has a long-term deleterious effect on a specific enzyme in a reagent layer ink, then these can also be separated between layers to prohibit loss of performance or sensitivity of the electrochemical test device that may occur due to loss of enzyme activity and/or an increase in background currents. Accordingly, analytical sensitivity and performance of an electrochemical test device is improved.

The sensing chemistry for the first working electrode may be for determining a concentration of glycerol and the NAD(P)$^+$-dependent dehydrogenase for the first working electrode may be glycerol dehydrogenase.

The sensing chemistry for the first working electrode may be for determining a concentration of β-hydroxybutyrate and the NAD(P)$^+$-dependent dehydrogenase for the first working electrode may be β-hydroxybutyrate dehydrogenase.

The diaphorase-containing layer may be adjacent the first working electrode and the second working electrode. The layer adjacent the electrode may not comprise the NAD(P)$^+$-dependent dehydrogenase, the electron transfer agent and the cofactor for the NAD(P)$^+$-dependent dehydrogenase.

The electron transfer agent, the NAD(P)$^+$-dependent dehydrogenase and the cofactor for the NAD(P)$^+$-dependent dehydrogenase may be disposed in a layer which is not adjacent the first working electrode.

The diaphorase-containing layer may also comprise the electron transfer agent.

The sensing chemistry for the first electrode may be disposed in two layers.

The diaphorase-containing layer may be a continuous layer.

The diaphorase-containing layer may be a discontinuous layer.

The first working electrode and the second working electrode may be for determining the concentration of the same analyte. The first working electrode and the second working electrode may be for determining the concentration of different analytes.

The electron transfer agent may be one or more of a Quinone derivative, an electrochemically active dye molecule, a transition metal containing anion, a transition metal containing cation or an electroactive organic molecule. The electron transfer agent may be a naphthoquinone.

The electron transfer agent may be ruthenium hexaammine trichloride.

The electron transfer agent may be a ruthenium- or osmium-based electron transfer agent. The ruthenium- or osmium-based electron transfer agent may be a complex of formula (1), $$[M(A)_x(B)_y](X)_n \quad (1)$$

wherein M is ruthenium or osmium, A is an amine ligand, each B is a ligand different to A, x is an integer selected from 1 to 5, y is an integer selected from 1 to 5, x+y is 6 or 8, n is an integer selected from 1 to 6, and X is any suitable counterion.

M may be ruthenium. For example, M may be Ru(II) or Ru(III). The oxidation state of the metal M in the complex may be selected to be 2+, 3+ or 4+.

A may be NRR'R", wherein R, R' and R" are independently selected from hydrogen or alkyl.

A may be NH$_3$. It will be appreciated that when x is two or more, all "A" may be the same.

Each B is a ligand different to A. It will be appreciated that when y is 2 or more, B may be the same or different. B may be independently selected from a halide or optionally substituted heteroaryl. When B is an optionally substituted heteroaryl, the heteroaryl may be optionally substituted with an optionally substituted C$_{1-6}$ alkyl. B may be a halide, and the halide may be selected from the group consisting of F$^-$, Cl$^-$, Br$^-$, I$^-$. B may be chloride. B may be pyridyl, or 4-methyl pyridyl.

It will be appreciated that A and B may be selected such that the overall charge on the complex of formula (1) is selected from the group +2, +1, 0, −1, −2 and −3.

The counterion X may be a counterion selected to lead to the charge neutrality of [M(A)$_x$(B)$_y$]. The counterion X may be selected from F$^-$, Cl$^-$, Br$^-$, I$^-$, PF$_6^-$.

The ruthenium complex may be [Ruthenium$^{III}$(NH$_3$)$_5$(pyridine)]X. The ruthenium complex may be [Ruthenium$^{III}$(NH$_3$)$_5$(4-methyl pyridine)]X. The ruthenium complex may be [Ruthenium$^{III}$(NH$_3$)$_5$Cl]X (ruthenium pentaammine chloride). The ruthenium complex may be [Ruthenium$^{III}$(NH$_3$)$_5$Cl].2Cl.

The ruthenium- or osmium-based electron agent may be a ruthenium-based electron transfer agent. The concentration of the ruthenium-based electron transfer agent in the sensing chemistry may be from 8% to 15% by weight before drying of the sensing chemistry.

Transition metal complexes of the present disclosure can be soluble in water or other aqueous solutions. In general, the transition metal complexes can be made soluble in aqueous solvents by having an appropriate counterion or ions, X. The solubility of the transition metal complex may be greater than about 0.025M at 25° C. in water.

The sensing chemistry may comprise between about 0.3%-2% (w/w) diaphorase. The sensing chemistry may comprise about 1% (w/w) diaphorase.

The diaphorase may be dissolved in a buffer such as, for example, phosphate or citrate. The buffer may be Tris buffer. The pH of the buffer may be about 7.

The sensing chemistry may comprise a phosphate or Tris buffer. The pH of the buffer may be in the range of about 6.5-7.5. For example, the pH of the buffer may be about 7. The pH of the buffer may be in the range of about 9.5-11. For example, the pH of the buffer may be about 10.5. The buffer may be of any suitable pH.

The diaphorase may have an enzyme activity range of from about 75 kU to 200 kU per 100 grams composition. The enzyme activity range is selected so that the analyte current does not depend on the level of enzyme activity in the composition and to avoid solubility issues for too high levels of diaphorase.

The sensing chemistry may comprise between about 0.07%-0.13% (w/w) flavin mononucleotide (FMN). The sensing chemistry may comprise 0.1% (w/w) FMN.

The sensing chemistry may comprise about 0.5%-3.5% (w/w), or 2.5%-3.5% (w/w), hydroxyethyl cellulose (HEC). The sensing chemistry may comprise 3% HEC.

In the context used herein, "about" may refer to a variation of ±10% of the numerical value.

The sensing chemistry for the second working electrode may comprise an oxidase. The sensing chemistry for the second working electrode may be for determining a concentration of lactate and the oxidase may be lactate oxidase. The sensing chemistry for the second working electrode may be for determining a concentration of glucose and the oxidase may be glucose oxidase.

The sensing chemistry for the second working electrode may comprise a dehydrogenase. The sensing chemistry for the second working electrode may comprise FAD-Glucose dehydrogenase and may comprise an appropriate cofactor. The sensing chemistry for the second working electrode may comprise PQQ-Glucose dehydrogenase and may comprise an appropriate cofactor.

The sensing chemistry for the second working electrode may comprise a diaphorase, an electron transfer agent, an $NAD(P)^+$-dependent dehydrogenase and a cofactor for the $NAD(P)^+$-dependent dehydrogenase.

The diaphorase-containing layer may be adjacent the first working electrode and the second working electrode and the layer adjacent the second working electrode may not comprise the $NAD(P)^+$-dependent dehydrogenase, the electron transfer agent and the cofactor for the $NAD(P)^+$-dependent dehydrogenase.

The diaphorase-containing layer may also comprise the electron transfer agent for the first working electrode and the second working electrode. The electron transfer agent for the first working electrode and the electron transfer agent for the second working electrode may be the same.

A method of manufacturing an electrochemical test device for determining a concentration of one or more analytes in a fluid sample is provided, the electrochemical test device comprising a set of electrodes including two or more working electrodes, each working electrode for determining the concentration of a corresponding analyte, and sensing chemistry for each working electrode, wherein the sensing chemistry for a first of the two or more working electrodes comprises a diaphorase, an electron transfer agent, an $NAD(P)^+$-dependent dehydrogenase and a cofactor for the $NAD(P)^+$-dependent dehydrogenase. The method comprises depositing diaphorase in a diaphorase-containing layer over the first working electrode and at least a second of the two or more working electrodes. The diaphorase-containing layer may be a continuous layer. The diaphorase-containing layer may be a discontinuous layer.

An apparatus is provided, the apparatus configured to determine the concentration of one or more analytes in a fluid sample applied to an electrochemical test device as described herein. The apparatus may comprise receiving circuitry for receiving a signal from the electrochemical test device such as an output signal generated from a fluid sample applied to the electrochemical test device. The apparatus may further comprise a memory storing instructions to determine the concentration of the analyte with reference to the received signal. The memory may also store data for the instructions to refer to, for example, data mapping the output signal to analyte concentration, or a function of the output signal to be calculated. The apparatus may further comprise a processor configured to perform the instructions stored in the memory.

FIG. 1 shows an apparatus in the form of a strip meter system 10. System 10 comprises a meter 12 for receiving an output signal from an electrochemical test device such as electrochemical test strip 14. Electrochemical test strip 14 comprises a set of electrodes which typically comprises one or more working electrodes (not shown in FIG. 1) and a counter/reference electrode, each of the working electrodes provided with sensing chemistry for reacting with at least one analyte of a fluid sample to be applied to electrochemical test strip 14. In this example, each of the one or more working electrodes has reagents coated thereon. The counter/reference electrode may also have reagents coated thereon. Meter 12 comprises receiving means 13 for receiving electrochemical test strip 14 and applying a potential difference to the working electrode(s) and the counter/reference electrode.

Meter 12 further comprises processing circuitry 15 for carrying various functions relating to the operation of meter 12. For example, processing circuitry 15 is configured to control operation of receiving means 13 so as to control application of a potential difference between the working electrode(s) and the counter/reference electrode. Processing circuitry 15 is further configured to process one or more output signals generated at test strip 14 and to control a display of messages on display 18. The processing circuitry may perform other functions. Meter 12 further comprises first and second memory storages 16a and 16b. Although two memory storages are shown, in other embodiments the memory storages may be combined to form a single memory storage, or meter 12 may comprise more than two memory storages. Meter 12 also comprises a display 18 for displaying readouts of measurements taken by meter 12.

When manufacturing an electrochemical test device such as electrochemical test strip 14 the device can be constructed in layers with different layers providing different features such as conductive tracks, electrode area definition and positioning of chemistry. Suitable manufacturing techniques may be used such as deposition techniques (e.g. printing such as thick-film printing methods including screen printing, rotary printing, serigraph printing, gravure printing and sub-microliter controlled volume drop on demand printing technologies) and adherence of layers, as will be apparent from the following.

Concerning the sensing chemistry applied to the electrodes, during manufacture a diaphorase-containing layer comprising diaphorase may be deposited over a first working electrode and at least a second working electrode of a plurality of working electrodes. Further reagent layers may be applied to each of the working electrodes as desired. The diaphorase-containing layer may be deposited continuously. The diaphorase-containing layer may be deposited as a discontinuous layer.

Figure 2:
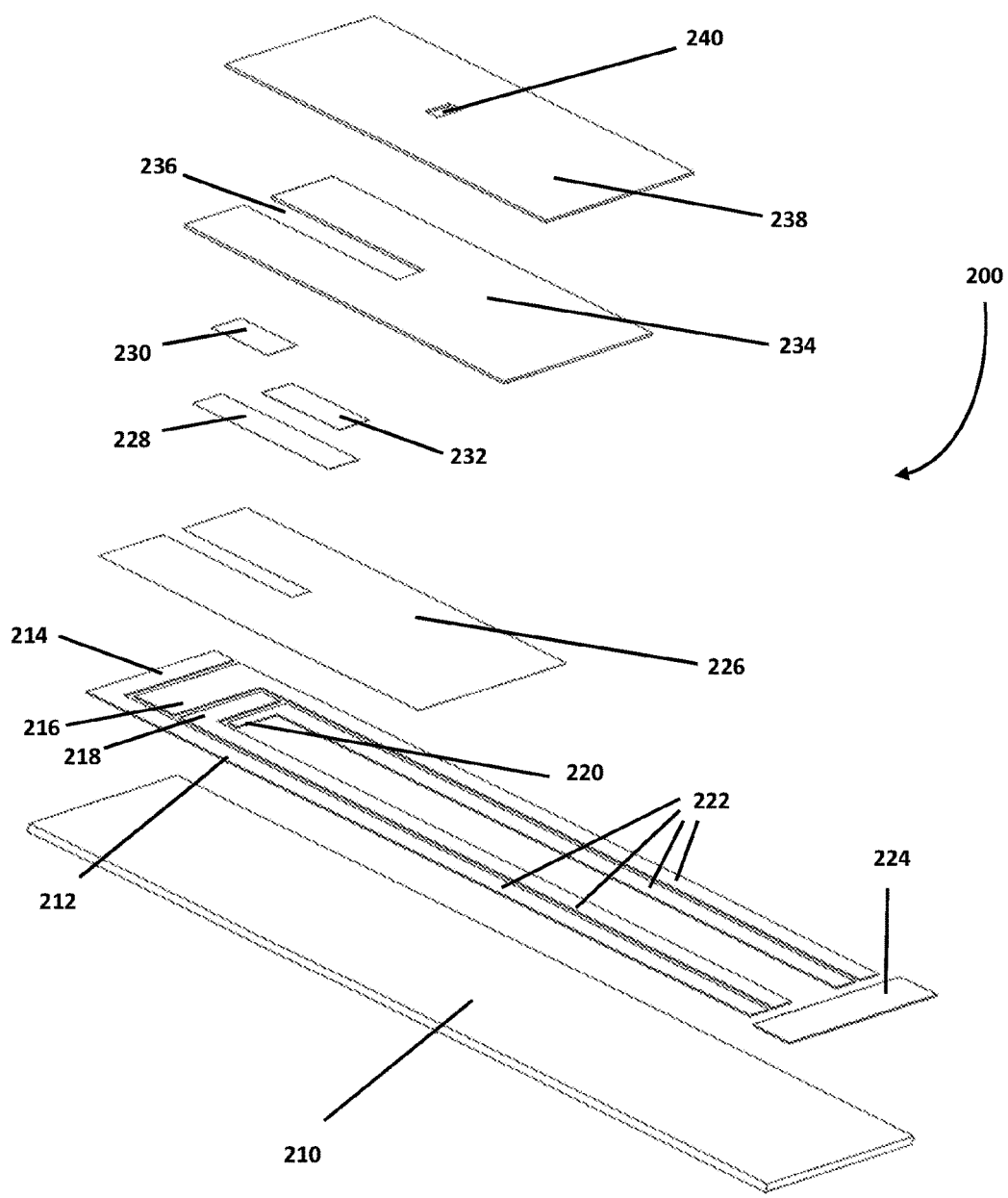
FIG. 2 shows an exploded view of an electrochemical test device.

FIG. 2 shows a perspective, exploded view of an electrochemical test device in the form of electrochemical test strip 200 according to a first example. This example will be described in relation to a received blood sample of around 0.5 μl in volume, although the electrochemical test strip 200 could be used with any suitable fluid sample. The electrochemical test strip 200 shown in FIG. 2 has an end-fill configuration i.e. the blood sample can be received at one end of the electrochemical test device 200.

The electrochemical test strip 200 comprises a support layer or substrate 210. Substrate 210 has a thickness of around 0.35 mm. The substrate 210, in this example, is made from polyester, although any suitable substrate may be used. The substrate 210 is thermally and dimensionally stable, with consistent properties such as thickness, surface roughness and surface energy.

Above the substrate 210 is the conductor layer 212. In this example, the conductor layer 212 is directly disposed upon the substrate 210 using carbon-based ink. In this example, the conductor layer 212 is printed directly onto the upper surface of the substrate 210. The conductor layer 212 may be printed onto the substrate 210 using screen printing, lithographic printing, tomographic printing, sub-microliter controlled volume drop on demand printing technologies, or any other suitable method of printing. The conductor layer comprises a set of electrodes including a first working electrode 214, counter/reference electrode 216, a second working electrode 218 and fill-sufficiency detect electrode 220. The conductor layer 212 further comprises a set of conductive tracks 222. In this example, the conductive tracks 222 extend along the longitudinal axis of the electrochemical test strip 200. The conductive tracks are suitable for electrically coupling the electrodes to a meter 12. The conductor layer 212 further comprises a switch-on bar 224 for activating a meter 12.

Above the conductor layer 212 is an insulating layer 226. The insulator layer 226 is made of an electrically insulating material, and is directly disposed upon the upper surface of the conductor layer 212. The insulator layer 226 is, in this example, made of a dielectric material and defines an interaction area. That is, the insulation layer 226 electrically insulates some portions of the conductor layer 212 from the layers situated above in the electrochemical test strip 200. Specially designed gaps in the insulator layer 226 expose some portions of the conductor layer 212 to the layers situated above in the electrochemical test strip 200. In this way, the insulator layer 226 defines which part or parts of the electrodes of the conductor layer 212 are able to come into contact with an applied blood sample for the measurement of the analyte.

Sensing chemistry is applied to the electrodes of the conductor layer 212. In this example, the sensing chemistry comprises three reagent layers 228, 230 and 232 which are applied to exposed electrode interaction areas after the insulator layer 226 is formed. A first reagent layer, or diaphorase-containing layer 228, is applied to both the first working electrode 214 and the second working electrode 218. In this example, the diaphorase-containing layer 228 is also applied to the counter/reference electrode 216 and the fill-sufficiency detect electrode 220. An additional reagent layer 230 is applied to the first working electrode 214 and at least a portion of the counter/reference electrode 216. An additional reagent layer 232 is applied to the second working electrode 218 and at least a portion of the counter/reference electrode 216. The reagent layers 228, 230 and 232 coat the exposed electrode interaction areas. The sensing chemistry of the reagent layers will be discussed in further detail below.

Above the insulator layer 226 is a spacer layer 234 formed of a polyester core. The spacer layer 234 defines a sample introduction channel 236, or measurement chamber, for introducing a blood sample to the conductor layer 212. The height of the sample introduction channel 236 is defined by the thickness of the spacer layer 234. The spacer layer 234 is formed of double sided adhesive tape which, in this example, is applied directly to the upper surface of the insulator layer 226. The sample introduction channel 236 is formed by providing a gap into the double sided adhesive tape of the spacer layer 234. The thickness of the spacer layer 234 is approximately 0.1 mm, which provides a good balance between the volume of the sample introduction channel 236 and the performance of the electrochemical test strip 200.

Above the spacer layer 234 is a cover layer 238. During manufacture, the spacer layer 234 and the cover layer 238 may be applied to the test strip 200 separately or as a single prelaminated layer, although in this example the cover layer 238 is a separate layer to the spacer layer 234. The cover layer 238 acts as a ceiling to the sample introduction channel 236, thereby substantially closing the sample introduction channel 236 from above. The cover layer 238 is formed of single sided tape and, in this example, is adhered directly to the upper surface of the spacer layer 234. The lower surface of the cover layer 238 has hydrophilic properties, which assist in drawing a blood sample into the sample introduction channel 236. The cover layer 238 further has a vent 240 suitable for venting air out of the sample introduction channel 236 to allow a blood sample to enter the sample introduction channel 236 via capillary action. The vent 240 is narrower than the sample introduction channel 236 so that air may easily vent from the sample introduction channel 236 but blood or any other fluid will not easily be able to pass through the vent 240.

In use, a fluid sample is provided to the electrochemical test device and a potential difference is applied across the fluid sample to generate a detectable output signal indicative of one or more analyte concentrations in the fluid sample. In this example, in use a blood sample is applied to the sample introduction channel 236 of the electrochemical test strip 200. Through capillary action, the blood is drawn into the sample introduction channel 230 to the electrodes 214, 216, 218 and 220 of the conductor layer 212. That is, the sample introduction channel 236 acts as a capillary channel. A potential difference is applied across the electrodes 214 and 216 and the blood sample, and the electrodes 218 and 216 and the blood sample, and output signals such as transient currents are generated from the blood sample. The characteristics of the output signal(s) can be used to determine the concentrations of one or more analytes, such as glucose, glycerol or β-hydroxybutyrate, in the blood sample.

Figure 3:
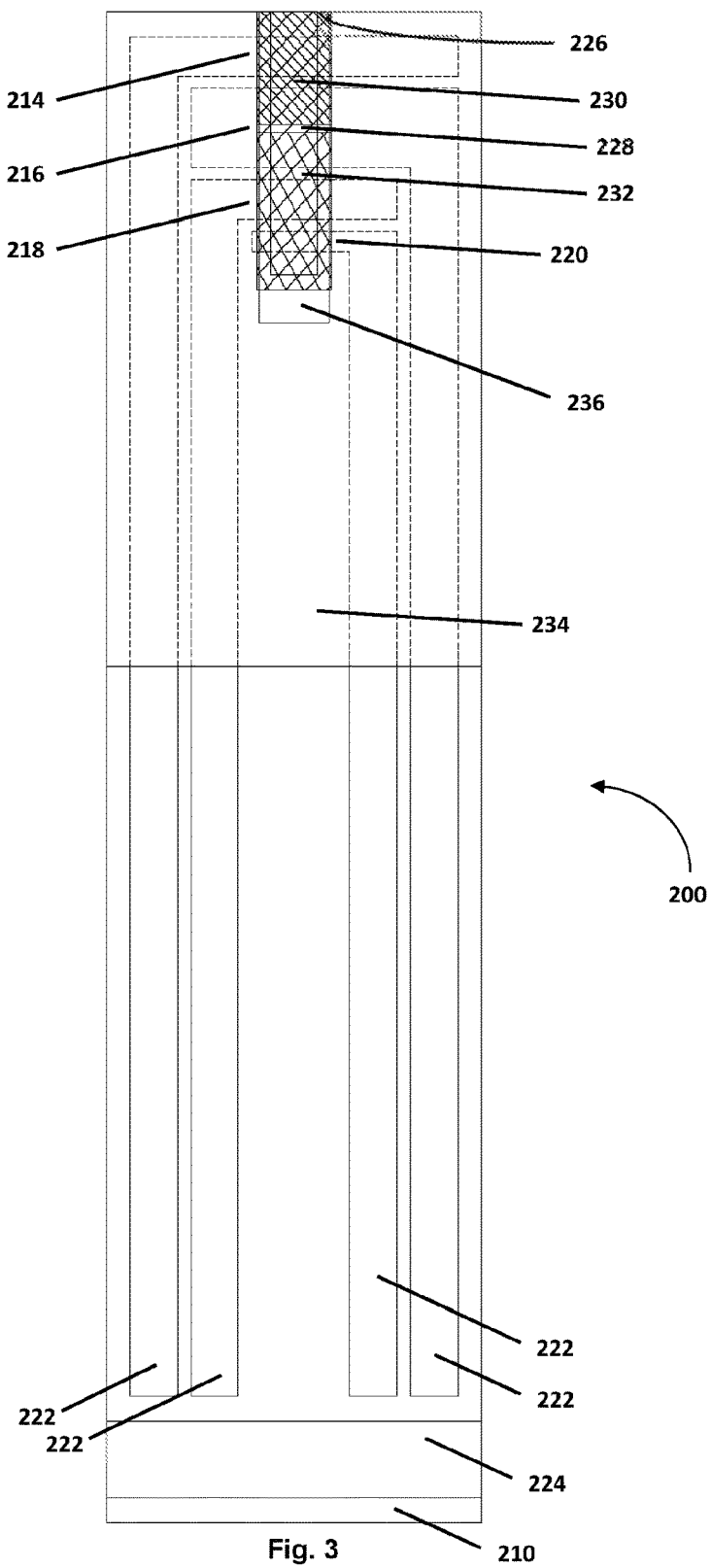
FIG. 3 shows a plan view of some layers of an electrochemical test device.

FIG. 3 depicts a plan view of some of the layers of the electrochemical test strip 200 of FIG. 2. In particular, FIG. 3 shows the substrate 210, the conductor layer 212, the insulator layer 226, the reagent layers 228, 230 and 232, and the spacer layer 234. The cover layer 238 is not shown in FIG. 3 for clarity. The diaphorase-containing layer 228 is applied to the exposed areas of the working electrodes 214 and 218, the counter/reference electrode 216 and the fill-sufficiency detect electrode 220. Reagent layers 230 and 232 each coat one of the working electrodes (214, 218) and partially coat the counter/reference electrode 216. In this example, reagent layer 232 additionally coats the fill-sufficiency detect electrode 220.

Sensing chemistry for the electrodes according to some examples will now be described with reference to FIGS. 4 to 6.

Figure 4:
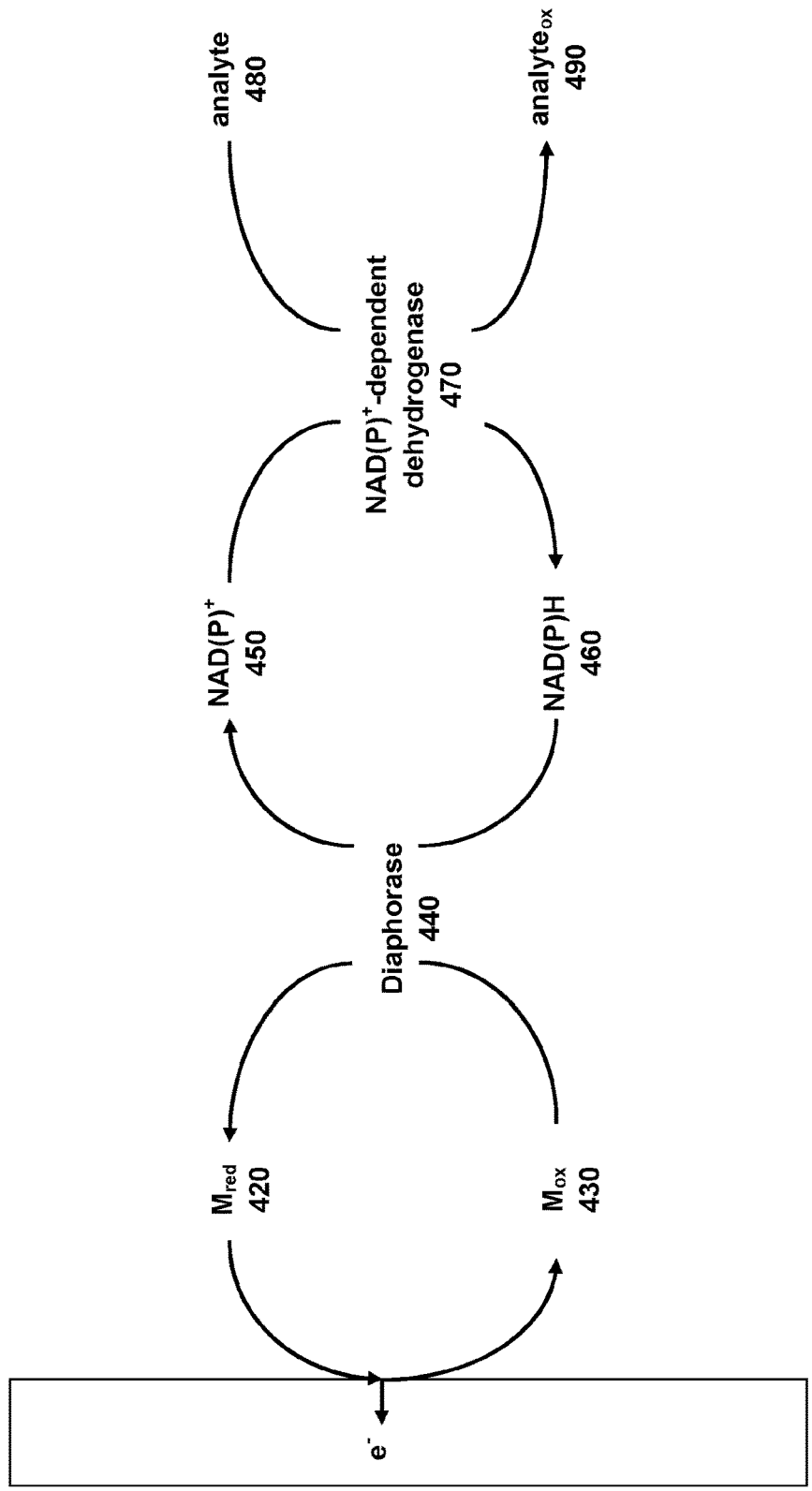
FIG. 4 illustrates bio-electrocatalysis at an electrode.

FIG. 4 is an illustration of bio-electrocatalysis at an electrode 410, which may correspond to first working electrode 214 above, according to an example. In this example, electrode 410 is coated with one or more layers of sensing chemistry suitable for reacting with an analyte 480 in a fluid sample. The sensing chemistry comprises a cofactor NAD(P)$^+$ 450, a NAD(P)$^+$-dependent dehydrogenase 470 for reacting with the analyte 480, a diaphorase 440 and an electron transfer agent or mediator (its reduced form $M_{red}$ 420 and its oxidised form $M_{ox}$ 430).

The diaphorase and the entrapped mediator (420, 430) carry out the following reactions:

$$NADH + H^+ + Mediator \rightarrow NAD^+ + \text{Reduced Mediator} \quad (2)$$

$$NADPH + H^+ + Mediator \rightarrow NADP^+ + \text{Reduced Mediator} \quad (3)$$

Either NADH or NADPH may be used as reductants.

With reference to FIG. 4, when in the presence of a fluid sample, a cofactor $NAD(P)^+$ 450 and an applied potential difference, an $NAD(P)^+$-dependent dehydrogenase 470 interacts with the analyte 480 of the fluid sample. NAD(P)H 460 is produced as a result of the interaction, as is an oxidised form of the analyte 490. In the presence of a diaphorase 440 (which acts as a catalyst), an oxidised form of a mediator 430 reacts with the NAD(P)H 460 at the active site of the diaphorase 440 to produce a reduced mediator 420 and $NAD(P)^+$ 450. The reduced form of the mediator 420 then transfers electrons ($e^-$) to the electrode 410.

In this way, the sensing chemistry applied to electrode 410 accomplishes the transfer of electrons from the fluid sample to the conducting electrode 410. A signal is thus generated to be detected by a strip meter.

Figure 5:
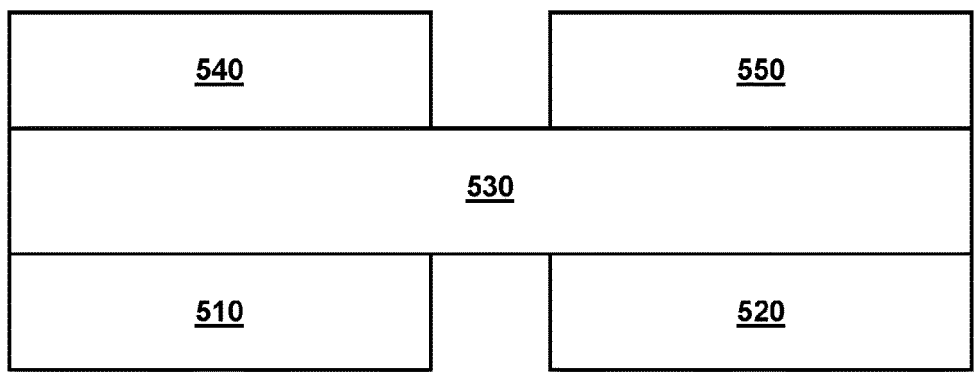
FIG. 5 shows reagent layers that may be applied to two working electrodes.

The sensing chemistry may be applied in layers to the electrodes as illustrated in FIG. 5. FIG. 5 is a schematic showing a first working electrode 510 and a second working electrode 520, each working electrode having sensing chemistry disposed thereon for detecting a corresponding analyte 480. The sensing chemistry includes a diaphorase-containing layer 530, which is common to both working electrodes 510, 520. The diaphorase-containing layer 530 is adjacent the first working electrode 510 and the second working electrode 520. An analyte-sensitive reagent layer 540 is applied to the first working electrode 510 by depositing the reagent layer 540 onto the diaphorase-containing layer 530 above the first electrode 510. Reagent layer 540 does not extend to the second working electrode 520. Reagent layer 540 comprises an electron transfer agent 420, 430, an $NAD(P)^+$-dependent dehydrogenase 470 and $NAD(P)^+$ 450. An analyte-sensitive reagent layer 550 is applied to the second working electrode 520 by depositing the reagent layer 550 onto the diaphorase-containing layer 530 above the second working electrode 520. Reagent layer 550 does not extend to the first working electrode 510. Reagent layer 550 also comprises an electron transfer agent 420, 430, an $NAD(P)^+$-dependent dehydrogenase 470 and a cofactor.

Additionally, each layer of the sensing chemistry comprises suitable buffers, surfactants and other additives. For example, the sensing chemistry may comprise one or more of a buffer, a gelling or thickening agent such as hydroxyethyl cellulose (HEC) or other cellulosic polymers, a rheology/viscosity modifier such as silica, flavin mononucleotide (FMN) for stabilising the diaphorase and a surfactant such as Tween 20.

Accordingly, in the presence of a fluid sample and an applied potential difference, enzymatic reactions may occur at each working electrode in order for an analyte to be detected at each working electrode. The first and second electrodes may be configured to detect the same analyte or different analytes. Any of the layers may coat a counter/reference electrode and/or a fill-sufficiency detect electrode also.

In a specific example, the first working electrode 510 is coated with sensing chemistry for detecting glycerol and the second working electrode 520 is coated with sensing chemistry for detecting β-hydroxybutyrate. A diaphorase-containing layer 530 extends across both the first working electrode 510 and the second working electrode 520. In this example, reagent layer 540 comprises glycerol dehydrogenase and $NAD^+$. Reagent layer 540 further comprises ruthenium pentaammine chloride, which acts as an electron transfer agent. Reagent layer 550 comprises β-hydroxybutyrate dehydrogenase and $NAD^+$. Reagent layer 550 also comprises ruthenium pentaammine chloride. In the presence of a potential difference across electrodes of the electrochemical test device, the glycerol dehydrogenase and $NAD^+$ in the reagent layer 540 of the first working electrode 510 interact with any glycerol that may be present in the fluid sample to produce an oxidised form of the glycerol and NADH. The ruthenium pentaammine chloride then transfers electrons to the first working electrode 510, as explained above in relation to FIG. 4. At the second working electrode 520, the β-hydroxybutyrate dehydrogenase and $NAD^+$ in reagent layer 550 interact with β-hydroxybutyrate in the fluid sample to produce NADH. The ruthenium pentaammine chloride then transfers electrons to the second working electrode 520.

Ruthenium pentaammine chloride has a number of benefits as an electron transfer agent. In particular, ruthenium pentaammine chloride has a standard redox potential of approximately −0.08 Volts. The standard redox potential for the $NAD(P)^+/NAD(P)H$ couple is approximately −0.315 Volts. Accordingly, ruthenium pentaammine chloride represents an overpotential with respect to the $NAD(P)^+/NAD(P)H$ redox couple of approximately 0.235 Volts. In order to achieve the high level of sensitivity that is required to measure, for example, glycerol (typically 0.05 mM) or blood ketones such as β-hydroxybutyrate (typically 0.1 mM) it is useful to choose a mediator with a low redox potential so that any interference due to the oxidation of opportunist species is reduced. Ruthenium pentaammine chloride is thus a good candidate for use in an electrode for measuring glycerol or β-hydroxybutyrate.

Although ruthenium pentaammine chloride has been used as the mediator in this example, any suitable mediator for the diaphorase catalysed reaction may be used. For example, ruthenium hexaammine trichloride may be used as an electron transfer agent. Ruthenium hexaammine trichloride has a standard redox potential of approximately 0.1 Volts, which corresponds to an overpotential with respect to the $NAD(P)^+/NAD(P)H$ redox couple of approximately 0.415 Volts. Accordingly, ruthenium hexaammine trichloride is a good candidate for use in an electrode for measuring glycerol, for which the sensitivity of the electrochemical test device is an issue. In addition it is known that this molecule is stable over time, reacting little to, for example, moisture, sunlight, temperatures experienced during manufacture and conditions experienced in storage. Accordingly, the sensitivity of an electrochemical test device incorporating this mediator will not deteriorate rapidly over time.

Another mediator that may be used is potassium ferricyanide. Potassium ferricyanide has a number of benefits as a mediator. In particular, potassium ferricyanide is highly water soluble, has a small molecular weight and fast homogeneous and heterogeneous kinetics. Accordingly potassium ferricyanide supports a large analyte measurement range.

Optionally, each of the reagent layers 540, 550 may use different mediators. For example, reagent layer 540 may comprise ruthenium pentaammine chloride and reagent layer 550 may comprise ruthenium hexaammine trichloride.

Although a first working electrode for measuring glycerol and a second working electrode for measuring β-hydroxybutyrate have been described, by using suitable dehydrogenases electrodes having sensing chemistry layered as in FIG. 5 may instead be configured to detect any combination of analytes in the fluid sample. For example, the electrochemical test device may be provided with sensing chemistry comprising flavin adenine dinucleotide (FAD)-dependent glucose dehydrogenase with its FAD cofactor, or pyrroloquinoline quinone (PQQ)-dependent glucose dehydrogenase with its PQQ cofactor.

Figure 6:
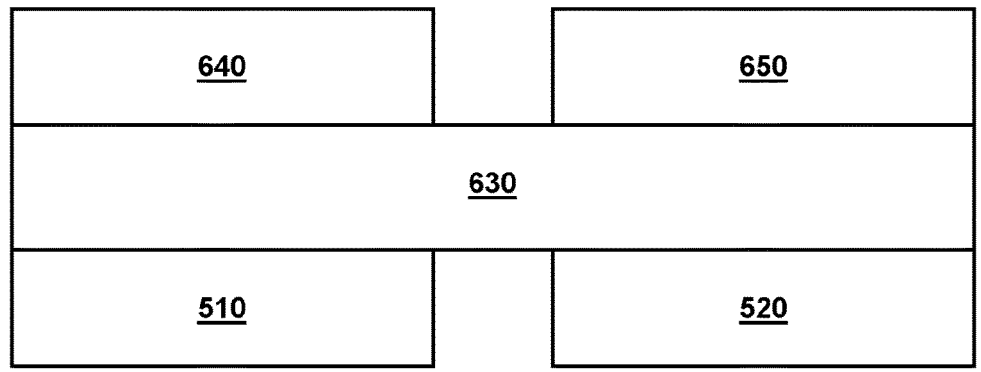
FIG. 6 shows reagent layers that may be applied to two working electrodes.

FIG. 6 is a schematic showing a first working electrode 510 and a second working electrode 520, each working electrode having sensing chemistry disposed thereon for detecting an analyte 480. The sensing chemistry includes a diaphorase-containing layer 630, which is common to both working electrodes 510, 520. The diaphorase-containing layer 630 is adjacent the first working electrode 510 and the second working electrode 520. The diaphorase-containing layer 630 further comprises an electron transfer agent. A further reagent layer 640 is applied to the first working electrode 510 by depositing the reagent layer 640 onto the diaphorase-containing layer 630 above the first working electrode 510. Reagent layer 640 does not extend to the second working electrode 520. Reagent layer 640 comprises an NAD(P)$^+$-dependent dehydrogenase 470 and NAD(P)$^+$ 450. A reagent layer 650 is applied to the second working electrode 520 by depositing the reagent layer 650 onto the diaphorase-containing layer 630 above the second working electrode 520. Reagent layer 650 does not extend to the first working electrode 510. Reagent layer 650 comprises an oxidase for interacting with an analyte and may further comprise an electron transfer agent.

Additionally, as with the examples described above in relation to FIG. 5, each layer of the sensing chemistry comprises suitable buffers, surfactants and other additives.

In a specific example, an electrochemical test device is configured to measure a concentration of lactate and a concentration of glycerol in a fluid sample. The electrochemical test device comprises two working electrodes. A first of the working electrodes 510 is coated with sensing chemistry for detecting glycerol. The second of the working electrodes 520 is coated with sensing chemistry for detecting lactate. The diaphorase-containing layer 630 comprises diaphorase and a ferricyanide anion such as potassium ferricyanide as an electron transfer agent. The diaphorase-containing layer 630 extends across the first 510 and the second 520 working electrodes. A further reagent layer 640 is applied to the first working electrode 510 and comprises glycerol dehydrogenase and NAD$^+$. A reagent layer 650 is applied to the second working electrode 520 and comprises lactate oxidase and potassium ferricyanide. The lactate oxidase does not require the diaphorase to transfer electrons to the second working electrode 520.

In the presence of a potential difference across electrodes, the glycerol dehydrogenase and NAD$^+$ in the reagent layer 640 of the first working electrode 510 interact with any glycerol that may be present in the fluid sample to produce an oxidised form of the glycerol and NADH. The potassium ferricyanide then transfers electrons to the electrode, as explained above in relation to FIG. 4. At the second working electrode 520, the lactate oxidase present in layer 640 interacts with any lactate in the fluid sample and the potassium ferricyanide transfers electrons to the second working electrode 520.

Although potassium ferricyanide has been used as the mediator in this example, any suitable mediator may be used. For example, layer 630 may comprise a quinone such as a naphthoquinone, or a ruthenium- or osmium-based compound. For example, ruthenium pentaammine chloride or ruthenium hexaammine trichloride may be used.

In a specific example, an electrochemical test device is configured to measure a concentration of β-hydroxybutyrate and a concentration of glucose in a fluid sample. As in the previous example, a diaphorase-containing layer 630 is applied across the first 510 and second 520 working electrodes, the diaphorase-containing layer further comprising an electron transfer agent. A reagent layer 640 comprising β-hydroxybutyrate dehydrogenase and NAD$^+$ is applied to the first working electrode 510. A reagent layer 650 comprising glucose oxidase is applied to the second working electrode 520. In the presence of a potential difference across electrodes, the β-hydroxybutyrate dehydrogenase at the first working electrode reacts with β-hydroxybutyrate in a fluid sample to provide and output signal. At the second working electrode 520, the glucose oxidase reacts with glucose in the fluid sample to provide an output signal. In this way, both β-hydroxybutyrate and glucose concentrations are measured using different reactions, each reaction occurring at a corresponding working electrode. It will be appreciated that the glucose oxidase in the above example can be substituted for FAD-glucose dehydrogenase enzyme and the electrochemical test device would still function.

Variations of the described embodiments are envisaged, for example, the features of all the disclosed embodiments may be combined in any way.

For example, an electrochemical test device may contain more layers than those disclosed in the preceding description. For example, an electrochemical test device may further comprise one or more bonding layers for bonding together one or more of the layers disclosed above. Additionally, some of the layers are not always necessary. For example, the insulator layer may be absent from the examples discussed above. The spacer layer may define the interaction area of the electrodes of the conductor layer beneath. The spacer layer may perform the dual role of receiving a fluid sample through a capillary channel and defining an interaction area for combining the fluid sample with the conductor layer. For example, the spacer layer can, with appropriate adhesive, define the active area/interaction area of the electrodes.

In the examples discussed above, a layer structure has been shown. The order in which each of the layers is formed may vary and any layer may, in some way, be configured so as to be in contact with any other layer.

The fluid sample may be a biological fluid. For example, the biological fluid may be blood, interstitial fluid, plasma, sweat, urine, lachrymal fluid, saliva or breath condensate. The analyte may be any analyte found in the fluid sample. For example, the analyte may be glucose, lactate, glycerol, cholesterol, or a ketone body such as β-hydroxybutyrate.

The electrochemical test device may be any suitable electrochemical test device. The electrochemical test device may be a test strip. In some examples the electrochemical test device may comprise a patch. Electrochemical test devices such as patches typically comprise a subcutaneous fluid extraction set and sensing chemistry for interaction with one or more analytes. The electrochemical test device may be a monitoring component which is configured to transmit an output signal to a separate device such as a meter, either wirelessly or through a wired connection. The electrochemical test device may comprise a continuous monitoring device or a semi-continuous monitoring device.

The electrochemical test device may be suitable for testing for multiple analytes. For example, the conductor layer may comprise a number of working electrodes, each working electrode featuring different sensing chemistry for detecting a different analyte. In particular, for each analyte there may be a dedicated working electrode of the conductor layer coated in reagents suitable for reacting with the analyte.

In the example discussed above in relation to FIG. 2, the electrochemical test device had an end-fill configuration. In other embodiments, an electrochemical test device has a side-fill configuration i.e. the fluid sample is received at the side of the electrochemical test device.

The electrochemical test device may be suitable for measuring any fluid sample volume and may be of a suitable corresponding size for the volume. For example the electrochemical test device described in relation to FIG. 2 was arranged to receive approximately 0.5 µl of blood. The electrochemical test device may be scaled so as to receive other volumes including, for example, between 0.5 µl and 5 µl of a fluid, or between 0.5 µl and 1 µl of a fluid. The electrochemical test device may be scaled so as to receive less than 0.5 µl of a fluid, for example around 0.2 µl or around 0.3 µl.

Although in the discussion above in relation to FIG. 2 a fill-sufficiency detect electrode 220 is present, the fill-sufficiency detect electrode need not be present. Additionally, the fill-sufficiency detect electrode 220 may or may not be coated in one or more reagent layers.

The sensing chemistry may be disposed upon any of the working electrodes, any of the working electrodes and counter/reference electrode, or any of the working electrodes, the counter/reference electrode and the fill-sufficiency detect electrode.

The diaphorase-containing layer may be applied to two or more working electrodes and can optionally be applied to the counter/reference electrode and/or the fill-sufficiency detect electrode. The diaphorase-containing layer may comprise other reagents such as an electron transfer agent. A diaphorase is provided in the diaphorase-containing layer but may also be provided in any one or more of the other layers of the sensing chemistry. The diaphorase-containing layer may be adjacent the working electrodes.

In the examples provided above, the conductor layer and the insulator layer are printed layers. The conductor layer and the insulator layer may be supplied using any suitable manufacturing technique. These include forms of printing, for example, screen printing, lithographic printing or tomographic printing. The conductor layer and the insulator layer need not be provided in the same way. Other suitable manufacturing techniques include etching, and/or sputtering, chemical vapour deposition or physical vapour deposition.

A conductor layer may be formed of any suitable conductor. For example, the conductor layer may be formed from a carbon based paste, such as a carbon/graphite paste, including graphene. The conductor layer may be formed of one or more metal based paste such as a gold, platinum or silver paste. Although the conductor layer 212 described above in relation to FIG. 2 comprises carbon-based ink, the conductors need not be formed from carbon based ink. For example, the electrodes may be formed of silver (Ag) or silver/silver chloride (Ag/AgCl). In some examples, the electrodes are formed of different conducting materials.

One or more of the working electrodes may, for example, be formed of carbon based ink whereas the counter/reference electrode may be formed of silver (Ag) or silver/silver chloride (Ag/AgCl).

The counter/reference electrode may be coated with a layer comprising an electron transfer agent. For example, an electrode formed from carbon based ink may be coated with a layer comprising mediator. The counter/reference electrode may not be coated in any sensing chemistry. For example, sensing chemistry may be absent from a counter/reference electrode formed of silver (Ag) or silver/silver chloride (Ag/AgCl).

The conductor layer may be of any suitable thickness. For example, the conductor layer may have a thickness greater than or equal to 0.005 mm and less than or equal to 0.030 mm.

The insulator layer may be formed of any suitable insulating material. For example, dielectric/insulation inks may be polymer loaded inks that are thermoplastic, thermoset or UV cured and that, when dried or cured, form a contiguous non-conductive layer. Examples include, Loctite EDAG PF 021 E&C and DuPont 5018.

In the examples discussed above, a polyester substrate layer was featured. Suitable substrate materials include polyester, polyimide, polystyrene, PVC, polycarbonate, glass and ceramic. When other layers are to be printed onto the substrate layer, the substrate layer has to be suitably printable for the chosen inks. The substrate must also be non-conductive. Typical thicknesses of the substrate layer range from 0.1 mm to 0.5 mm e.g. 0.35 mm. Glass and ceramic can be thicker as these are easier to handle with increased thickness. Thinner polymer substrates may be more difficult for the end user to use. Thicker substrates may offer some handling benefits.

The spacer layer may be formed of any suitable material. For example, the spacer layer may be made from a polyester core with a thin layer of PSA (Pressure Sensitive Adhesive) on either side. These adhesives can be the same or different depending on which layer is to be adhered to which side of the spacer layer.

Although in the examples above the thickness of the spacer layer was 0.1 mm, the thickness may vary. A typical range for the spacer layer thickness is 0.005-0.030 mm. Lower thicknesses may affect sensor performance and higher thicknesses would increase the volume of the sample introduction channel. A thickness of an adhesive on the spacer layer may contribute to the rigidity of the spacer layer.

Typically a spacer layer has a high volume resistivity. For example the volume resistivity may be greater than $1 \times 10^9$ $\Omega$cm.

Other variations of the spacer layer are envisaged.

The sample introduction chamber may be provided along the longitudinal axis of the electrochemical device. The sample introduction chamber may be provided along the transverse axis of the electrochemical test device.

The vent may be of any suitable configuration for venting air from the sample introduction chamber. For example, the vent may comprise an air passageway in the cover. The vent may comprise an air passageway in the spacer layer. Optionally, air may be vented from the sample introduction chamber through one or more air passageways below the spacer layer, such as through the conductor layer or the insulator layer. Air may be vented into a sealed chamber.

In the examples above, two reagent layers are applied to each working electrode. There may be more than two reagent layers. For example, there may be a number of intermediate layers between a layer adjacent the electrode and a layer for coming into contact with a fluid sample.

In the disclosure above, an NAD(P)$^+$-dependent dehydrogenase for reacting with an analyte was described. Examples of suitable NAD(P)$^+$-dependent dehydrogenases include glycerol dehydrogenase, Glycerol-3-phosphate dehydrogenase, D-3-Hydroxybutyrate dehydrogenase, Cholesterol Dehydrogenase, Lactate Dehydrogenase, D-Lactate dehydrogenase, Malate Dehydrogenase, Alcohol Dehydrogenase and Leucine dehydrogenase.

Many electron transfer agents or mediators may be used with the examples described above. For example, suitable mediators include quinones such as benzoquinone, dyes such as 2,6-dichlorophenolindophenol and tetrazolium dyes, and redox couples such as ferricyanide anions and ferricinium cations, phenazine ethosulfate, phenazine methosulfate, 2-methyl-1,4-naphthoquinone and ferrocene derivatives.

The electron transfer agent may comprise a suitable quinone, for example a naphthoquinone derivative. The naphthoquinone derivative may be a 1,2 naphthoquinone derivative or a 1,4 naphthoquinone derivative. For example, the electron transfer agent may comprise 1,4 naphthoquinone-2-mercapto methyl carboxylic acid which has a standard redox potential of around −0.355V. The electron transfer agent may comprise 1,4 naphthoquinone-2-mercapto benzoic acid, which has a standard redox potential of around −0.345V. The electron transfer agent may comprise 1,2 naphthoquinone-4-sulphonate, which has a standard redox potential of around −0.214V. The electron transfer agent may comprise 1,4 naphthoquinone-2-mercapto methyl sulphonate. Also other suitable isomers of the above listed compounds are known which have similarly low standard redox potentials.

Both ruthenium hexaammine trichloride and ruthenium pentaammine chloride were mentioned above as suitable mediators. Other ruthenium based complexes that may be used as a mediator include ruthenium pentaammine pyridine and ruthenium pentaammine 4-methyl pyridine.

Suitable electron transfer agents may be osmium based compounds. For example, osmium phendione may be used as a mediator. [Os(4,4'-dimethyl-2,2'-bipyridine)$_2$] may also be used as a mediator, as may [(trpy)(bpy)M-OH]$^{2+}$ (M=Os; trpy=2,2',2''-terpyridine; bpy-2,2'-bipyridine).

Any electron transfer agent may be used with any of the sensing chemistry configurations described above in relation to FIGS. 4 to 6.

Further techniques may be used to enhance the sensitivity of any measurements made by the electrochemical test device. For example, the electrochemical test device may be configured to include a suitable delay before applying the voltage to the electrodes, during which the concentration of the measurand is allowed to accumulate at the working electrode surface.

Whilst the above examples have been described primarily in the context of an electrochemical test device for measuring a concentration of an analyte in a bodily fluid, it may equally be used in other fields, for example in health and fitness, food, drink, bio-security applications and environmental sample monitoring. The examples described herein may equally be used in the context of animal/veterinary medicine and fitness (including dogs and horses).

The above embodiments have been described by way of example only, and the described embodiments are to be considered in all respects only as illustrative and not restrictive. It will be appreciated that variations of the described embodiments may be made without departing from the scope of the invention.

The invention claimed is:

1. An electrochemical test device for determining a concentration of one or more analytes in a fluid sample, the electrochemical test device comprising a set of electrodes including two or more working electrodes, each working electrode for determining the concentration of a corresponding analyte, and sensing chemistry for each working electrode, wherein the sensing chemistry for a first of the two or more working electrodes comprises a diaphorase, an electron transfer agent, an NAD(P)$^+$-dependent dehydrogenase and a cofactor for the NAD(P)$^+$-dependent dehydrogenase, wherein at least some of the diaphorase for the first working electrode is disposed in a diaphorase-containing layer which extends over the first working electrode and at least a second of the two or more working electrodes.

2. An electrochemical test device according to claim 1, wherein the sensing chemistry for the first working electrode is for determining a concentration of glycerol and the NAD(P)$^+$-dependent dehydrogenase for the first working electrode is glycerol dehydrogenase.

3. An electrochemical test device according to claim 1, wherein the sensing chemistry for the first working electrode is for determining a concentration of β-hydroxybutyrate and the NAD(P)$^+$-dependent dehydrogenase for the first working electrode is β-hydroxybutyrate dehydrogenase.

4. An electrochemical test device according to claim 1, wherein the diaphorase-containing layer is adjacent the first working electrode and the second working electrode; and optionally
wherein the layer adjacent the electrode does not comprise the NAD(P)$^+$-dependent dehydrogenase, the electron transfer agent and the cofactor for the NAD(P)$^+$-dependent dehydrogenase.

5. An electrochemical test device according to claim 1, wherein the sensing chemistry for the second working electrode comprises an oxidase; and optionally
wherein the sensing chemistry for the second working electrode is for determining a concentration of lactate and the oxidase is lactate oxidase; or
wherein the sensing chemistry for the second working electrode is for determining a concentration of glucose and the oxidase is glucose oxidase.

6. An electrochemical test device according to claim 1, wherein the electron transfer agent, the NAD(P)$^+$-dependent dehydrogenase and the cofactor for the NAD(P)$^+$-dependent dehydrogenase are disposed in a layer which is not adjacent the first working electrode; and/or,
wherein the sensing chemistry for the first electrode is disposed in two layers; and/or
wherein the diaphorase-containing layer is a continuous layer.

7. An electrochemical test device according to claim 1, wherein the diaphorase-containing layer also comprises the electron transfer agent.

8. An electrochemical test device according to claim 1, wherein the sensing chemistry for the second working electrode comprises a dehydrogenase; and optionally
wherein the sensing chemistry for the second working electrode comprises FAD-Glucose dehydrogenase; or
wherein the sensing chemistry for the second working electrode comprises PQQ-Glucose dehydrogenase.

9. An electrochemical test device according to claim 1, wherein the sensing chemistry for the second working electrode comprises a diaphorase, an electron transfer agent, an NAD(P)$^+$-dependent dehydrogenase and a cofactor for the NAD(P)$^+$-dependent dehydrogenase; and optionally
wherein the diaphorase-containing layer is adjacent the first working electrode and the second working electrode and the layer adjacent the second working electrode does not comprise the NAD(P)$^+$-dependent dehydrogenase, the electron transfer agent and the cofactor for the NAD(P)$^+$-dependent dehydrogenase; or wherein the diaphorase-containing layer also comprises the electron transfer agent for the first working electrode and the second working electrode; and/or wherein the electron transfer agent for the first working electrode and the electron transfer agent for the second working electrode are the same.

10. An electrochemical test device according to claim 1, wherein the diaphorase-containing layer is a discontinuous layer.

11. An electrochemical test device according to claim 1, wherein the first working electrode and the second working electrode are for determining the concentration of the same analyte.

12. An electrochemical test device according to claim 1, wherein the first working electrode and the second working electrode are for determining the concentration of different analytes.

13. An electrochemical test device according to claim 1, wherein the electron transfer agent is a quinone; and optionally wherein the electron transfer agent is a naphthoquinone derivative; and optionally wherein the naphthoquinone derivative is a 1,2 naphthoquinone derivative or a 1,4 naphthoquinone derivative; or wherein the naphthoquinone derivative is 1,4 naphthoquinone-2-mercapto methyl carboxylic acid; or wherein the naphthoquinone derivative is 1,4 naphthoquinone-2-mercapto benzoic acid; or wherein the naphthoquinone derivative is 1,2 naphthoquinone-4-sulphonate; or wherein the naphthoquinone derivative is 1,4 naphthoquinone-2-mercapto methyl sulphonate.

14. An electrochemical test device according to claim 1, wherein the electron transfer agent is ruthenium hexaammine trichloride; or wherein the electron transfer agent is a ruthenium- or osmium-based electron transfer agent.

15. An electrochemical test device according to claim 14, wherein the ruthenium- or osmium-based electron transfer agent is a complex of formula I,

[M(A)$x$(B)$y$](X)$n$  Formula I wherein

M is ruthenium or osmium;

A is an amine ligand;

each B is a ligand different to A;

x is an integer selected from 1 to 5;

y is an integer selected from 1 to 5;

x+y is 6 or 8;

n is an integer selected from 1 to 6;

X is any suitable counterion: and optionally wherein M is ruthenium; and/or wherein B is halide, or optionally substituted heteroaryl; and/or wherein the oxidation state of the metal is selected to be 2+ or 3+.

16. An electrochemical test device according to claim 15, wherein B is chloride; or wherein B is an optionally substituted pyridine; or wherein B is pyridine or 4-methyl pyridine.

17. An electrochemical test device according to claim 15, wherein the ruthenium complex is selected from [Ruthenium$^{III}$(NH$_3$)$_5$(pyridine)]X, [Ruthenium$^{III}$(NH$_3$)$_5$ (4-methyl pyridine)]X, and [Ruthenium$^{III}$(NH$_3$)$_5$Cl]X; and/or wherein the counterion X is selected from F$^-$, Cl$^-$, Br$^-$, I$^-$, PF$_6^-$; and optionally wherein the ruthenium complex is [Ruthenium$^{III}$(NH$_3$)$_5$Cl].2Cl.

18. An apparatus configured to determine the concentration of an analyte in a fluid sample applied to an electrochemical test device according claim 1.

19. A method of manufacturing an electrochemical test device for determining a concentration of one or more analytes in a fluid sample, the electrochemical test device comprising a set of electrodes including two or more working electrodes, each working electrode for determining the concentration of a corresponding analyte, and sensing chemistry for each working electrode, wherein the sensing chemistry for a first of the two or more working electrodes comprises a diaphorase, an electron transfer agent, an NAD(P)$^+$-dependent dehydrogenase and a cofactor for the NAD(P)$^+$-dependent dehydrogenase, the method comprising:

depositing diaphorase in a diaphorase-containing layer over the first working electrode and at least a second of the two or more working electrodes.

20. A method according to claim 19, wherein the diaphorase-containing layer is a continuous layer; or wherein the diaphorase-containing layer is a discontinuous layer.

* * * * *